(12) United States Patent
Alemi

(10) Patent No.: US 8,145,583 B2
(45) Date of Patent: Mar. 27, 2012

(54) TAILORING MEDICATION TO INDIVIDUAL CHARACTERISTICS

(75) Inventor: Farrokh Alemi, McLean, VA (US)

(73) Assignee: George Mason Intellectual Properties, Inc., Fairfax, VA (US)

( * ) Notice: Subject to any disclaimer, the term of this patent is extended or adjusted under 35 U.S.C. 154(b) by 610 days.

(21) Appl. No.: 12/274,633

(22) Filed: Nov. 20, 2008

(65) Prior Publication Data

US 2009/0132460 A1    May 21, 2009

Related U.S. Application Data

(60) Provisional application No. 60/989,171, filed on Nov. 20, 2007.

(51) Int. Cl.
*G06F 17/00* (2006.01)
*G06N 5/00* (2006.01)

(52) U.S. Cl. ............... 706/45; 706/46; 706/47; 706/62; 600/300; 600/301; 600/408

(58) Field of Classification Search .................. None
See application file for complete search history.

(56) References Cited

U.S. PATENT DOCUMENTS

| | | | | |
|---|---|---|---|---|
| 7,315,825 B2* | 1/2008 | Rosenfeld et al. | ................ | 705/2 |
| 7,730,063 B2* | 6/2010 | Eder | ........................... | 707/736 |
| 2003/0101076 A1* | 5/2003 | Zaleski | ............................ | 705/2 |
| 2004/0122706 A1* | 6/2004 | Walker et al. | .................... | 705/2 |
| 2005/0251424 A1* | 11/2005 | Sanders et al. | ................... | 705/3 |
| 2008/0015894 A1* | 1/2008 | Miller et al. | ..................... | 705/2 |
| 2009/0054740 A1* | 2/2009 | Gudmundsson et al. | ..... | 600/300 |
| 2010/0324874 A9* | 12/2010 | Bangs et al. | .................. | 703/11 |

OTHER PUBLICATIONS

Amos Tversky, "Preference, Belief, and Similarity", A Bradford Book: The MIT Press, 2003, pp. 1-39.*
Unknown Author. The Navy Standard Score. Student Naval Aviator Training and Administration Manual, [online], [retrieved on Jul. 23, 2011]. Retrieved from the Internet <URL: http://www.tpub.com/content/aviation2/1500.4Fwch1&2&3&4&5/1500.4Fwch1&2&3&4&50155.htm>.*

* cited by examiner

*Primary Examiner* — Omar Fernandez Rivas
(74) *Attorney, Agent, or Firm* — David Grossman; David Yee (57) ABSTRACT

Disclosed is a medical outcome prediction tool that predicts an individual patient's medical outcomes by identifying patients having a same disease; selecting a set of characteristics unique to an individual; determining the similarities between the individual and other cases; and calculating the expected outcome for the individual that is proportional to a weighted sum of outcomes of similar cases. The similarities can be determined by calculating the number of matches between the individual and cases over the set of characteristics, and using that result to determine a similarity score.

10 Claims, 6 Drawing Sheets

TAILORING MEDICATION TO INDIVIDUAL CHARACTERISTICS

CROSS REFERENCE TO RELATED APPLICATIONS

The present application claims the benefit of provisional patent application Ser. No. 60/989,171 to Alemi, filed on Nov. 20, 2007, entitled "Tailoring Medication to Individual Characteristics," which is hereby incorporated by reference.

BACKGROUND OF THE INVENTION

Personalized medicine is built on the notion that there is an inherent contradiction of going from studies of groups of patients to advice and recommendations for an individual patient. It involves tools and statistics to help clinicians advise one patient at a time, even in contradiction to results of group studies. A great part of these tools and statistics involve the genetic profile of the patient and other information (e.g. co-morbidity, concurrent medication, allergies), which can be used to tailor diagnoses and treatments based on patients' unique characteristics.

Yet, it is generally difficult to deduce from population/group studies what will work for an individual patient. Some medication may work for some patients but not for others. A multitude of factors may account for any variation in medical effects. Examples include the type of medication, dosage, absorption rate, severity of illness, drug-drug interactions, allelic combination of a patient's genes encoding detoxification enzymes, age, nutritional status, comorbidities, etc. Given the complexity of determining the right medication for patients, health providers need a tool for providing more effective prescriptions beyond the trial and error methods.

Current predictive models supposedly predict medical outcomes for individuals based on the use of a certain medicine. For example, Langheier et al. (US Pat. Appl'n US 2006/0173663 A1) discloses an optimal intervention predictive model that selects a mathematical model and estimates parameters relating the intervention to the outcome.

However, Langheier presents a complicated and less accurate approach that relies on discovering the relationship among various factors at the group level and then applying the findings to the individual at hand. Group level relationships mask what might work for individual patients. A medication may not work for the average patient but may work for some subset of patients or for the particular patient at hand.

Another approach often used in examining the effectiveness of treatments is analysis of variance. Here, statistical significance can be tested by calculating Fischer F test statistic:

$$F = \text{(variance of the group means)}/\text{(mean of the within group variances)} \quad (1)$$

However, this assumption does not seem reasonable in the context of personalized care as using information across patients to find what works for one patient seems antithetical to the goals of personalized care. Both the variance of mean of treatment and the mean of within group variances, are calculated from experiences of others, many of whom are not like the patient at hand and their data are irrelevant to the case at hand. The analysis is faulty not because it is mathematically or logically incorrect but because it uses data that is irrelevant to task at hand. This approach assumes that what works for the average patient will also work for the patient at hand, which contradicts the very goal of personalized medicine. Neuhauser points out that there is no such thing as an average patient; all patients differ from the average reported in the literature in some unique ways and average study results are of little guidance for individual patients.

Some statisticians may propose selecting increasingly small treatment groups, so all members of the group are essentially the same as the patient at hand. The idea is that by looking at a handful of characteristics (such as 5 or 10) of the patient, a sub-group in the population database that share all these features can be found. Therefore, calculating the variance of this subgroup will be relevant to the case at hand. But in practice, any attempt to redefine treatment groups so that it matches the patient at hand is inevitably futile as when the number of features used increases. When genetic and phenotypic information are included, the number of cases within the group will go down, often to one or no case.

A number of scientists have even tried to resolve this problem by suggesting experimental studies of N of 1. One approach is to use sequential analysis. In this approach, one person may be observed over time and treatment may be modified (typically in small steps) until a statistically significant treatment is found. But the problems with statistical approaches to personalized medicine is not limited to restrictions to studies of N of 1. A more fundamental approach is the utility of statistical significance and mathematical modeling of causes of improvement.

When it comes to personalized medicine, it is important to change current methods so that it reflects the new constraints that would work for one patient. Hence, what is needed is a simplified and accurate prediction model that does not rely on selecting various models to foresee a potential medical outcome. Also, what is needed is a strategy that detects whether a particular medication works for the patient at hand—independent of whether it works for others or for an average patient.

DETAILED DESCRIPTION OF THE INVENTION

The present invention relates to a prediction model based on individual characteristics. In one embodiment, the present invention applies to predicting medical outcomes for a particular individual.

Figure 1:
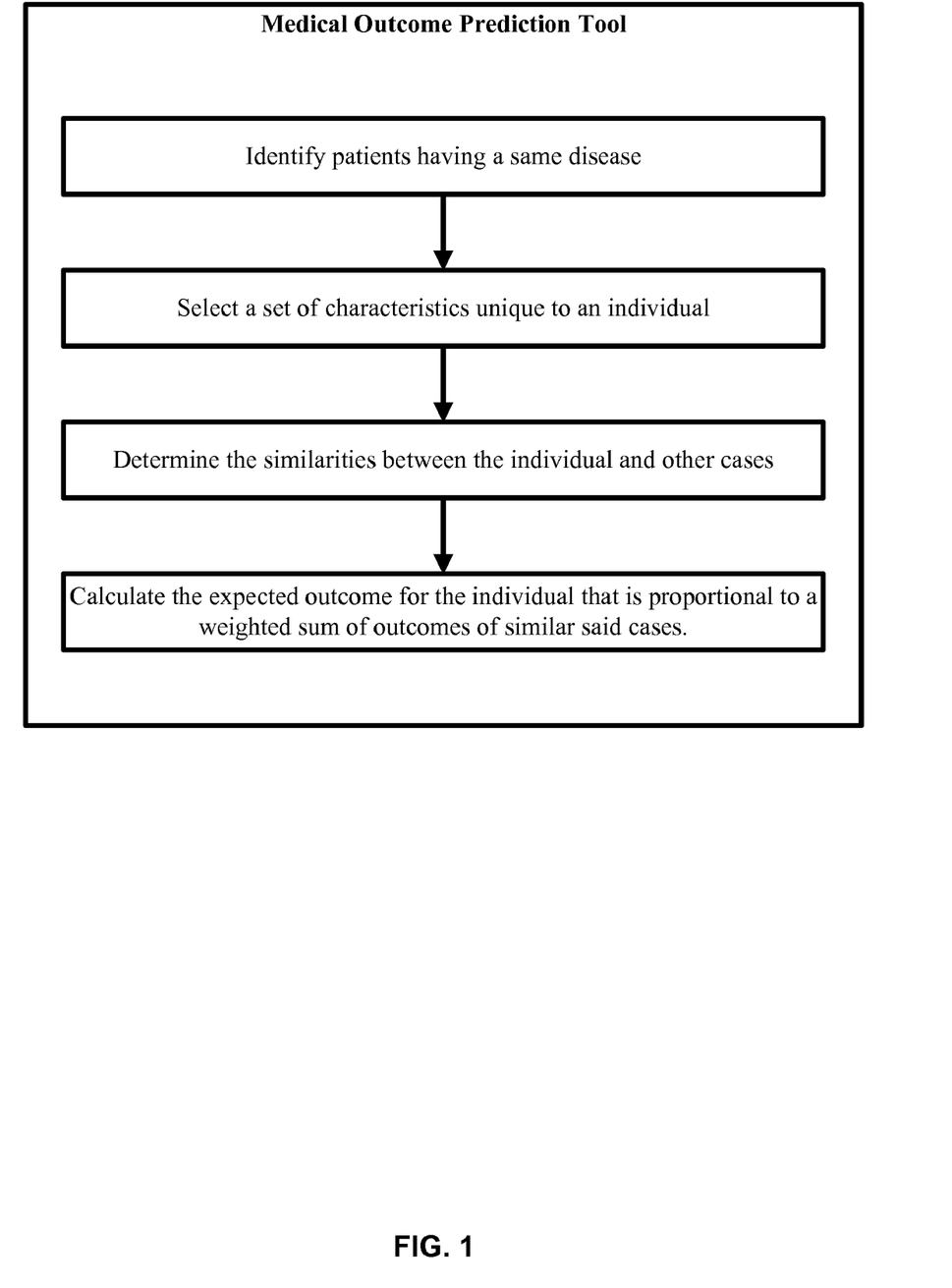
FIG. 1 shows a diagram of instructions of the medical outcome prediction tool.

Referring to the figures, FIG. 1 discloses a medical outcome prediction tool that includes instructions for a program for predicting an individual patient's medical outcomes. These instructions include identifying patients having a same disease; selecting a set of characteristics unique to an individual; determining the similarities between said individual and other cases; and calculating the expected outcome for said individual that is proportional to a weighted sum of outcomes of similar said cases.

It should be noted that the word "disease" is used interchangeably with the word "illness". Disease/illness is any condition that causes or has a negative effect on a person's health, as determined by a physician, pharmacist, dentist, clinician, or as identified by a set of health/health-related codes. Examples of health/health-related codes include, but are not limited to, the International Classification of Diseases (ICD) (such as ICD, Ninth Revision, (ICD-9)/ICD, Ninth Revision, Clinical Modification (ICD-9-CM)), Healthcare Common Procedure Coding System (HCPCS), Current Procedural Terminology (CPT), National Drug Code (NDC), etc.

The medical outcome prediction tool is implementable in a computer or tangible computer readable medium. Tangible computer readable medium means any physical object or computer element that can store and/or execute computer instructions. Examples of tangible computer readable medium include, but not limited to, a compact disc (CD), digital versatile disc (DVD), blu-ray disc (BD), usb floppy drive, floppy disk, random access memory (RAM), read-only memory (ROM), erasable programmable read-only memory (EPROM), optical fiber, etc. It should be noted that the tangible computer readable medium may even be paper or other suitable medium in which the instructions can be electronically captured, such as optical scanning. Where optical scanning occurs, the instructions may be compiled, interpreted, or otherwise processed in a suitable manner, if necessary, and then stored in computer memory.

Alternatively, it may be a plugin or part of a software code that can be included in, or downloaded and installed into a computer application. As a plugin, it may be embeddable in any kind of computer document, such as a webpage, word document, pdf file, mp3 file, etc.

As one embodiment, disease identification can be based on an electronic health record (EHR). EHRs are simply individual health records in a digitized format that can be accessed via a computer or computer-based system over a network. EHRs are designed to keep information about each encounter with the patient. When the patient shows again, the information form the previous visits can be retrieved. For example, EHRs may include a person's health characteristics, medical history, past and current diagnoses, lab reports and results, x-rays, photographs, prescribed medication, billing and insurance information, contact information, demographics, etc.

Information recorded in EHRs can be used for a multitude of reasons in addition to being stored for future retrieval. For instance, they can be used to benchmark clinical practices, set pay for performance incentives, identify trends in illness in a community, and measure quality of care.

Additionally, EHRs can provide a remarkable advantage for analysis. Nonlimiting benefits include providing access to data on a large number of patients, organizing terms in a standardized manner (e.g., ICD-9, ICD-9-CM, etc.), and allowing data on an entire population to be available so as to avoid sampling.

As another embodiment, EHRs may be used to select an individual's characteristics. Those selected may be based upon their uniqueness to the individual. Alternatively, they may be different from an average patient in the practice.

Nonlimiting examples of characteristics include race, gender, age, symptoms, side effects, allergies, dietary habits, physical and/or mental condition(s), etc. It is expected that some characteristics may overlap or be partially redundant when compared to other individuals. For example, it is well known that any person who lists being pregnant as a characteristic is also a female.

Because many characteristics can and do overlap, the present invention is said to be a robust prediction model. Thus, the prediction model taught herein should not be confused as an optimal prediction model.

Statistical analysis of differences across patients tends to lead to a set of characteristics that are optimal in predicting outcomes. Moreover, correlated and redundant characteristics are often dropped from the analysis. In contrast, the present invention includes any characteristic that distinguishes the client from other patients—whether redundant or not.

Figure 2:
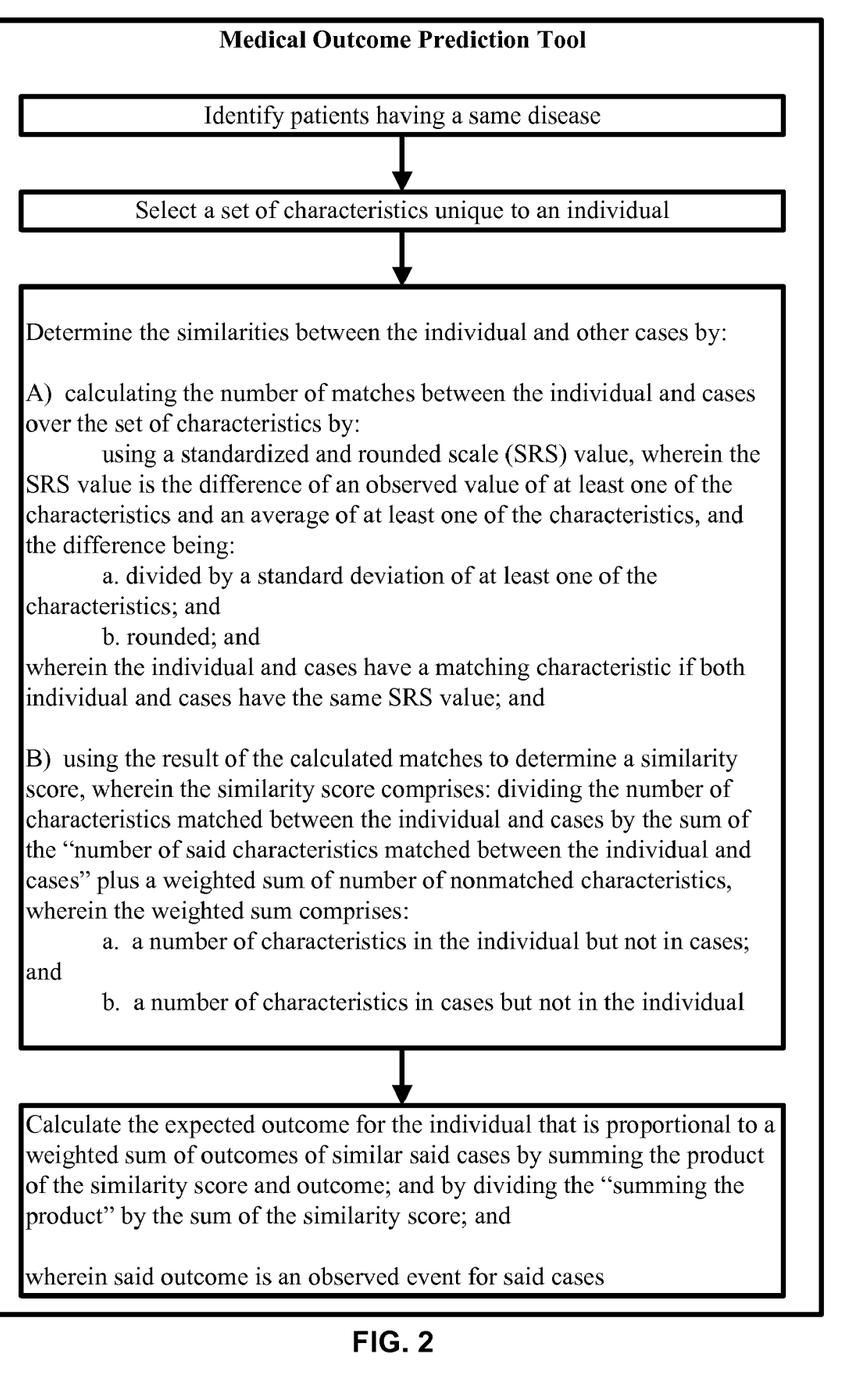
FIG. 2 shows another diagram of additional instructions of the medical outcome prediction tool.

FIG. 2 shows an embodiment of how to determine the similarities between an individual and cases. First, the number of matches between the individual and cases over the set of characteristics are calculated. Afterwards, the result of such calculation is used to determine a similarity score.

To calculate matches, a standardized and rounded scale (SRS) value may be used. The SRS value may be the rounded dividend of (1) the difference of an observed value of at least one of the characteristics and an average of at least one of the characteristics, and (2) the standard deviation of at least one of the characteristics. When both the individual and cases have the same SRS value, then the individual and cases are said to have a matching characteristic.

Once matches have been determined, the similarity score may be identified. To calculate this score, the number of matching characteristics between the individual and cases is divided by the sum of (1) the number of matching characteristics between the individual and cases and (2) a weighted sum of nonmatching characteristics. This weighted sum of nonmatching characteristics comprise a number of characteristics in the individual that is not shown in said cases, and the number of characteristics in cases that is not shown in the individual.

The expected outcome can be calculated by summing the product of said similarity score and said outcome, and then dividing that product by the sum of the similarity score. Outcome is defined as an observed event for the cases. Examples of observed events include, but are not limited to, mortality, morbidity, relapse, and failure to comply with medication.

Figure 3:
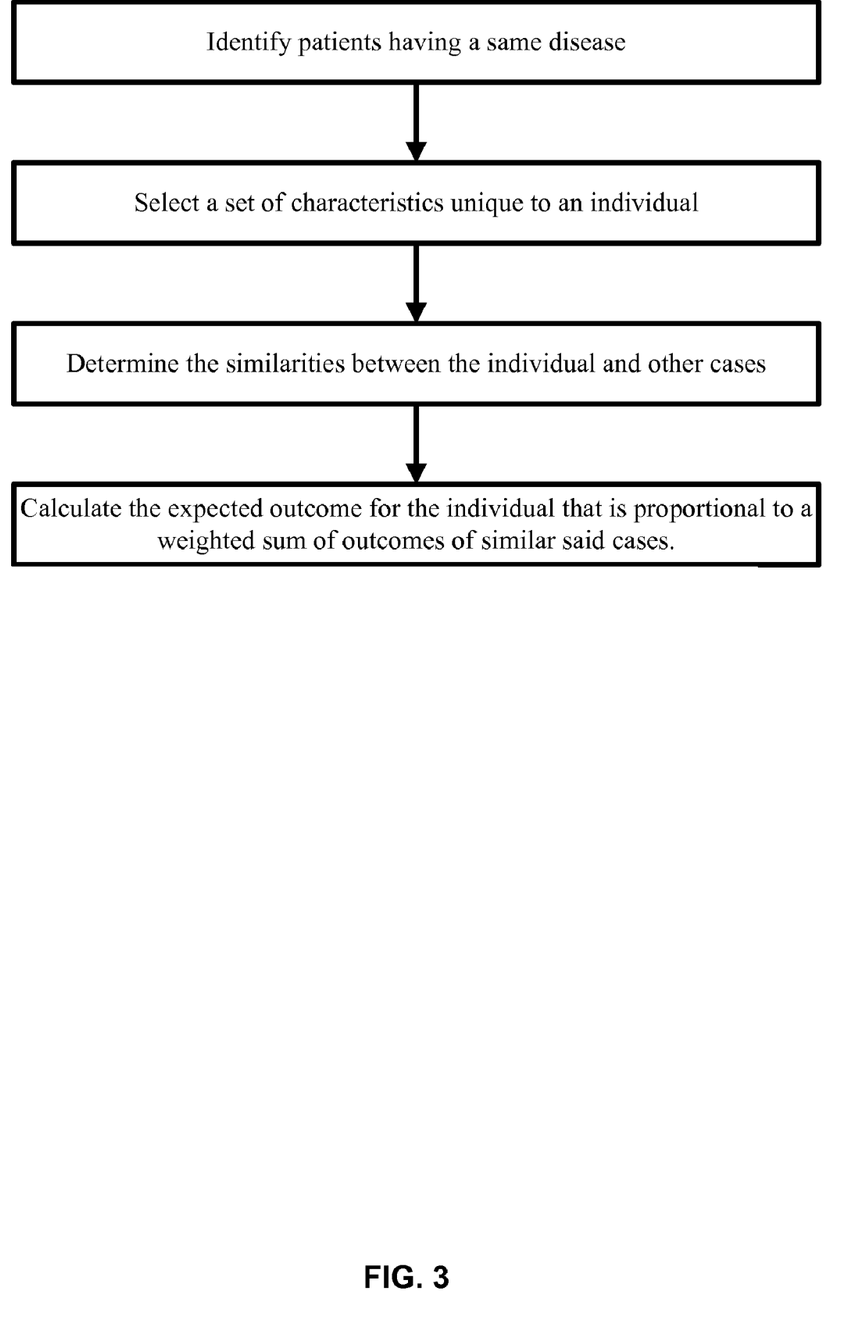
FIG. 3 shows a flow diagram of predicting medical outcomes.
Figure 4:
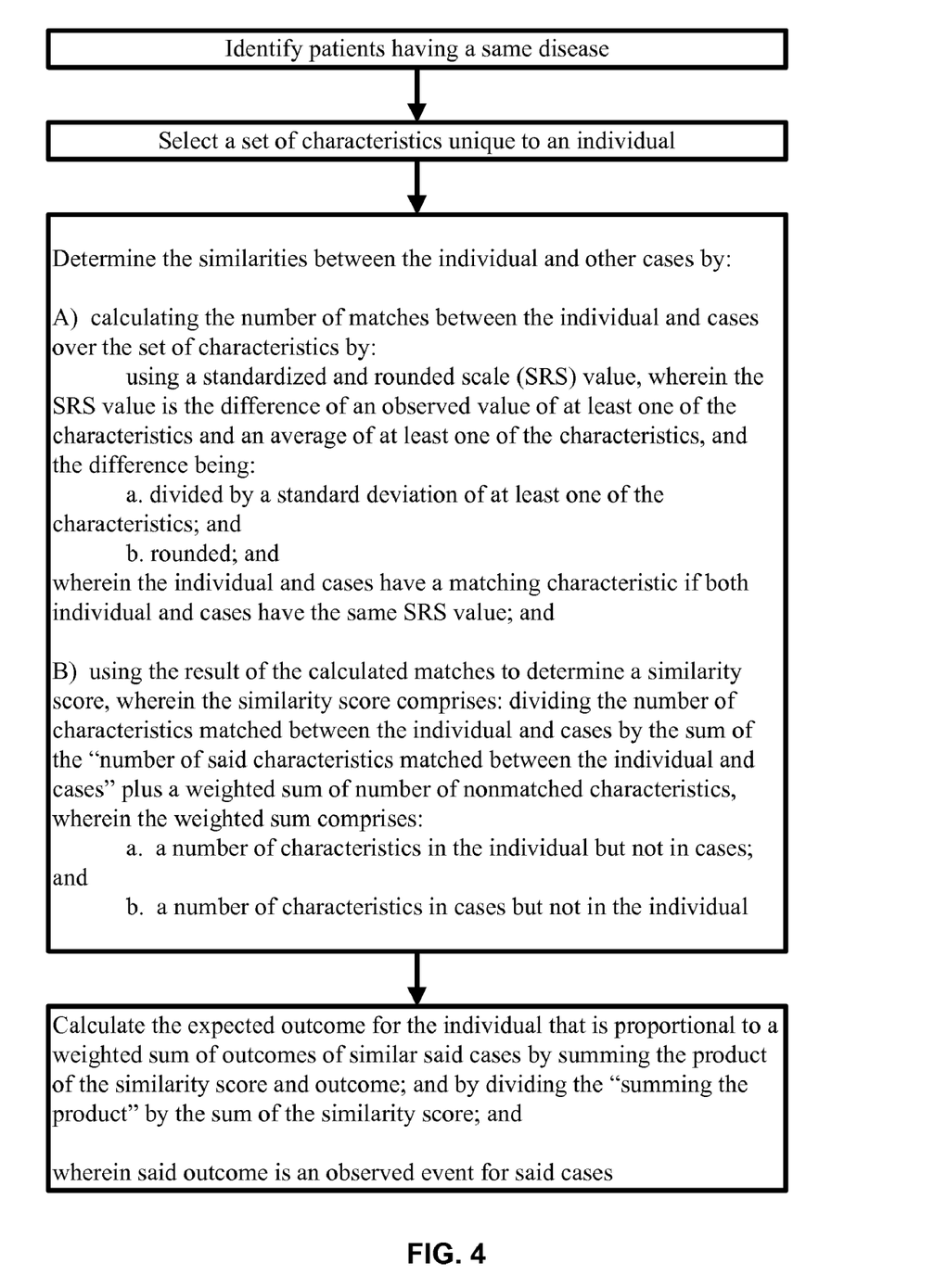
FIG. 4 shows another flow diagram of predicting medical outcomes.

Similarly, referring to FIGS. 3 and 4, the present invention also discloses a method for predicting an individual patient's medical outcomes. This method can be implemented in the medical outcome prediction tool. Additionally, this method can be implemented in any tangible computer readable medium, computer, or network. Alternatively, it can be practiced by hand. These steps include identifying patients having a same disease; selecting a set of characteristics unique to an individual; determining the similarities between said individual and other cases; and calculating the expected outcome for said individual that is proportional to a weighted sum of outcomes of similar said cases.

The similarities can be determined by calculating the number of matches between the individual and cases over the set of characteristics by using a SRS value as described above and using that result of to determine a similarity score, also as described above.

The expected outcome can be calculated just as described above.

Figure 5:
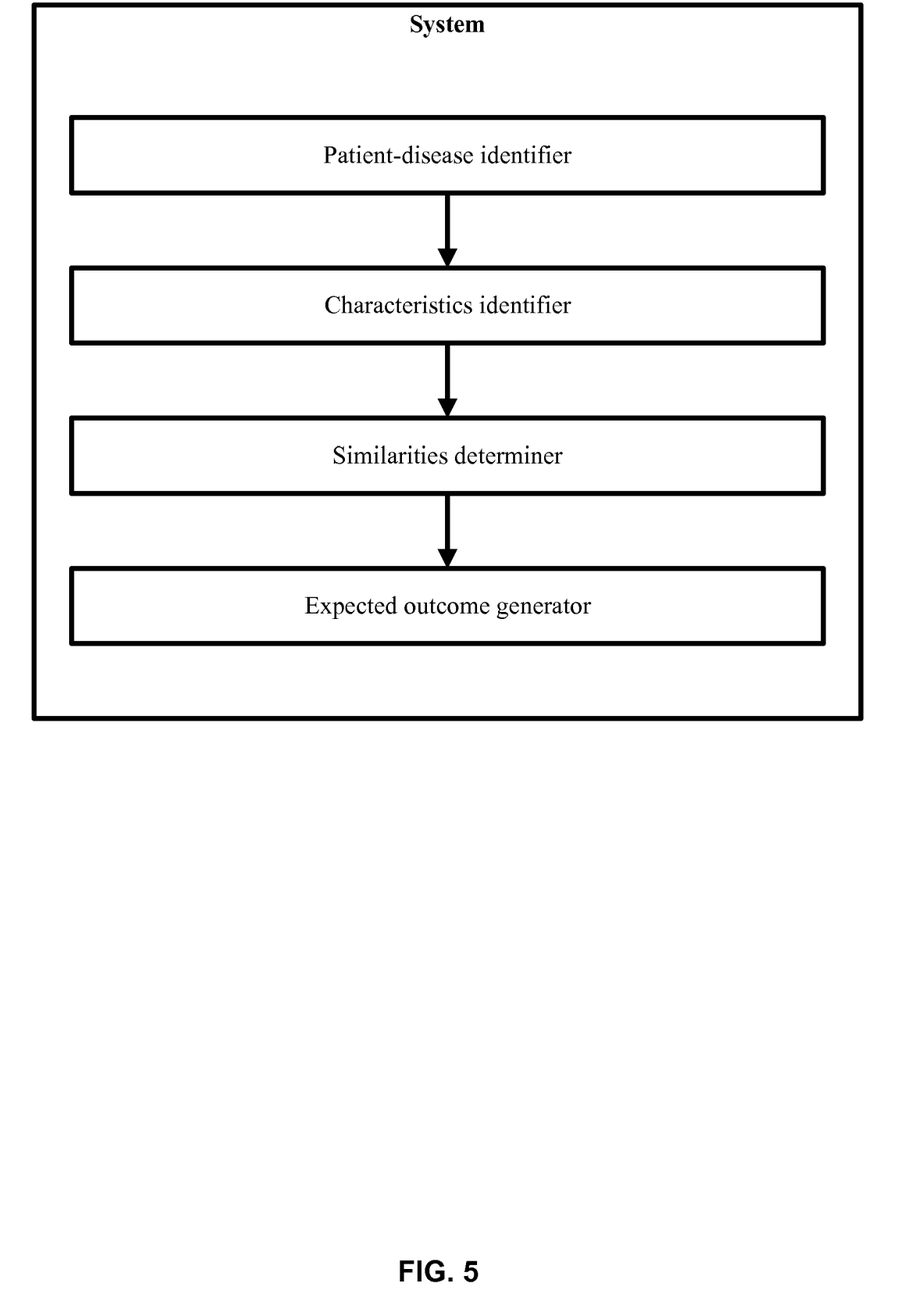
FIG. 5 shows a block diagram of a system that predicts medical outcomes.
Figure 6:
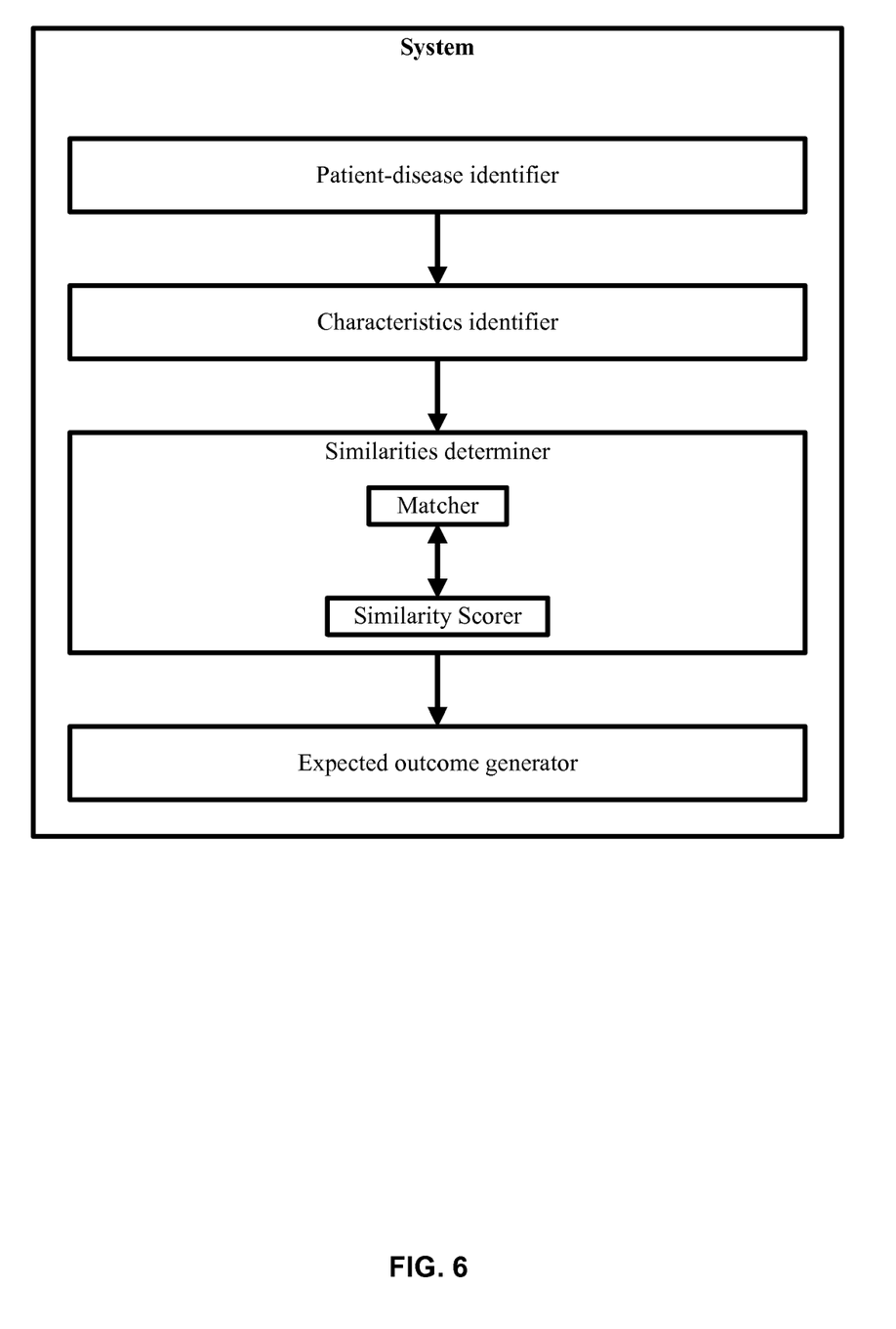
FIG. 6 shows another block diagram of a system that predicts medical outcomes.

In addition to a medical outcome prediction tool, the present invention also discloses a system, as seen in FIGS. 5 and 6, with components for predicting an individual patient's medical outcomes. These components include a patient-disease identifier; a characteristics identifier; a similarities determiner; and an expected outcome generator.

The patient-disease identifier can be configured for identifying patients having a same disease within an electronic health record.

The characteristics identifier can be configured for selecting a set of characteristics unique to an individual (or different from average patient in the practice) using an electronic health record.

The similarities determiner can be configured for determining the similarities between the individual and other cases. This determination can be achieved by using a matcher and a similarity scorer.

The matcher can be configured for calculating the number of matches between the individual and cases over the set of characteristics by using a standardized and rounded scale (SRS) value. The SRS value is the difference between an observed value of at least one of the characteristics and an average of at least one of the characteristics. This difference can be divided by a standard deviation of at least one of the characteristics Furthermore, this difference can also be rounded. The individual and cases are said to have a matching characteristic if both individual and cases have the same SRS value.

The similarity scorer can be configured for determining a similarity score by using the result of the calculated matches. The similarity score may be determined by dividing the number of characteristics matched between the individual and cases by the sum of such number plus a weighted sum of a number of nonmatched characteristics. The weighted sum may comprise a number of characteristics in the individual but not in the cases, and a number of the characteristics in the cases but not in the individual.

The expected outcome generator can be configured for calculating the expected outcome for the individual that is proportional to a weighted sum of outcomes of similar cases. This weighted sum can be identified by summing the product of the similarity score and the outcome, and by dividing the summed product by the sum of the similarity score. The expected outcome is an observed event for the cases.

Predicting Outcomes

1. Identify patients who have the same disease.

Identification can be accomplished by selecting all patients with the same diagnosis within the EHR. Data about patients reside in many different tables and/or different databases. The algorithm here does not require all data to reside in the same table and can be carried out on several different databases simultaneously. Results may be merged at the end of an analysis.

The following embodied structured query language (SQL) command exemplify how patients with the same diagnosis can be selected from a data source containing visit diagnosis, such as in the form of ICD-9, ICD-9-CM, or even CPT codes:

```
SELECT Visits.PrimaryDx, Visits.PatientID FROM Visits WHERE
(((Visits.PrimaryDx="Specific Disease Code"));
```

2. Select the patient characteristics that affect the impact of medication on outcomes.

The procedures for predicting medical outcomes for patients according to their characteristics are based on any available data on the patients. Minimally, data is needed on patient demographics. In particular, some diets and genetic reactions to medication may be traced to specific ethnic groups, and thus it remains important to have information on the patient's ethnicity. Additionally, other data that is minimally needed include: patient's concurrent medication, patient's allergies, patient's concurrent co-morbidities, patient's history of illness, and patient's key genetic and protein markers.

Generally, the more information that is available on the patient, the better it is to find similar patients for deducing potential reactions to certain medications. It should be noted that there is no need to select among various patient characteristics a priori. More importantly, the nature of these kinds of procedures is not based on a priori rules. But, to reduce unnecessary computations, the present invention allows for analyses to be limited to key findings where literature has stated to be important in medication selection.

To accomplish such feature, data items to be selected should be the ones that are the most informative about patient outcomes. Hence, such data include data items with likelihood ratios as different from 1 as possible. For instance, the likelihood ratio for datum should be equal to the prevalence of datum i among unsuccessful trials of the medication divided by the prevalence of datum i among unsuccessful trials of the medication.

For each patient, as well as for each trial of a medication and type of medication, success depends on both taking the medication as prescribed (medication compliance) and the effectiveness of the medication (medication impact). In some diseases, medication impact is not clear (e.g., there is generally no marker for recovery from depression that is clear cut and that can be used in the analysis). Under such circumstances, medication compliance is used as a surrogate measure of eventual improvement in patient outcomes. Thus, the likelihood ratio of a particular datum i may be calculated by dividing the prevalence of datum i among trials with good compliance over the prevalence of datum i among trials with poor compliance.

Also, it should be noted that patients can go through a trial and error period before they settle on a specific medication. Each trial and error serves as a separate observation in calculation of the likelihood ratios. Thus, for example, if an elderly patient goes through three antidepressants before settling on one that works for her, then the likelihood ratio for this particular case may be: Likelihood ratio for age >65=1/3.

3. Check if the patient at hand shares a characteristic with others in the database.

The present invention operates on matching the case at hand to cases within a database (such as an EHR). When two patients have the same characteristics (e.g., gender, history of diabetes, etc.), the match between the two is simple: either they share the same characteristic or they do not. When patients' characteristics are measured on continuous scales (e.g., blood pressure, age, etc.), it may be more difficult to match the two. In such circumstances, a standardized and rounded scale (SRS) value may be used.

As an embodiment of the present invention, the SRS values used is:

$$\text{SRS for patient } i = \text{Round}\left(\frac{O_i - A}{S}\right). \quad (2)$$

$O_i$ refers to the observed scale value for patient i. A refers to the average of the scale value for all patients. S refers to the standard deviation of the scale value for all patients. The function Round removes digits passed the decimal.

A match is to occur when two patients being compared to each other have the same SRS value (e.g., when the scale value for the two patients is less than one standard deviation different from each other). In this fashion, both continuous and discrete variables can be used to find matching patients within the database.

The following SQL code shows an embodiment of how the average and standard deviation of a continuous scale is calculated in step (3) above:

```
SELECT Avg([Patient Characteristics].ContinuousScale) AS
AvgOfContinuousScale, StDev([Patient Characteristics].ContinuousScale)
AS
StDevOfContinuousScale FROM [Patient Characteristics];
```

The following SQL code shows another embodiment of the present invention of how the SRS variable can be created for the patients (or cases) in the database:

```
SELECT [Patient Characteristics].[Patient ID], [Patient
Characteristics].DiscreteScale. Round((([ContinuousScale]-[Step 3
Calculate Average]!AvgOfContinuousScale) / [Step 3 Calculate
Average]!StDevOfContinuousScale,0) AS SRS FROM [Step 3 Calculate
Average], [Patient Characteristics];
```

As yet a further embodiment, the following SQL code, using the same procedure above for the patients (or cases) in the database, can be applied to the patient at hand:

```
SELECT [Patient at Hand].Patient ID, [Patient at Hand].Discrete. Round (
([ContinuousCharacteristic]-[Step 3 Calculate
Average]!AvgOfContinuousScale) / [Step 3 Calculate
Average]!StDevOf ContinuousScale,0) AS SRS FROM [Patient at Hand],
[Step 3 Calculate Average];
```

4. Calculate the similarity of the patient at hand to all other patients (cases) within the EHR's database.

Many investigators are looking for a genetic or other biomarker that can help them diagnose or treat a patient. For example, investigators have been looking for an enzyme that could suggest a depressed patient is likely to benefit from a particular antidepressant. The idea is that, if there is a sensitive and a specific genetic marker, patients who have this biomarker can be targeted to receive the intervention. But a biomarker is not necessarily needed and the search for such markers is helpful to the scientist but not necessary for the clinician.

If the purpose is to help one patient then one easy way is to find out what has worked with similar patients in the past. Similarity of two or more patients can be proportionally established to the number of genes, proteins, and other features the two or more patients share.

As one embodiment, the judgment of similarities of patients in a database to the patient at hand may be based on a well established feature matching protocol as proposed by Tversky. This protocol is:

$$S_{i,j} = \frac{f_{i,j}}{f_{i,j} + af_{i,not\,j} + bf_{not\,i,j}}. \quad (3)$$

The suffix "i" indicates the patient at hand. The suffix "j" indicates patient "j" in the database. "$S_{i,j}$" refers to the similarity of the $j^{th}$ patient in the database to the patient at hand. The variable "$f_{i,j}$" refers to the number of features (e.g., genes, proteins, phenotypes, etc.) shared between $j^{th}$ patient in the database and the patient at hand. For discrete features, two or more features are shared if they are the same. For continuous variables, two or more features are shared if they are within one standard deviation of each other.

The variable "$f_{i,\,not\,j}$" refers to the number of features (e.g., genes, proteins, phenotypes, etc.) in the patent at hand but not in the $j^{th}$ patient in the database. The variable "$f_{not\,i,j}$" refers to the number of features (e.g., genes, proteins, phenotypes, etc.) not in the patent at hand but in the $j^{th}$ patient in the database. The constant "a" is typically set to 0.20. This value generally puts a larger emphasis on missing the patient's characteristics than on missing the characteristics of the case in the database. The constant "b" is typically set to 0.80.

A great deal of scientific evidence suggests that human judgment of similarity tends to follow Tversky's suggested feature matching model. This method of measuring similarity generally puts a larger emphasis on missing the characteristics of the index case, namely the patient at hand, than on missing the characteristics of the comparison cases, namely the patients in the database. Such emphasis may lead to an asymmetric similarity score. For instance, when comparing children's features to parents' features, it will make children more similar to parents than the reverse.

As an embodiment, the following SQL shows commands for counting the number of features matched or missed:

```
SELECT IIf([Step 3 Patient at Hand SRS values]!Discrete=[Step 3
SRS]!DiscreteScale,1,0) + IIf([Step 3 Patient at Hand SRS values]!SRS=
[Step 3 SRS]!SRS,1,0) AS MatchedFeatures, IIf([Step 3 Patient at Hand
SRS values]!Discrete="No" And [Step 3 SRS]!DiscreteScale=
"Yes",1,0) + IIf([Step 3 Patient at Hand SRS values]!SRS=0 And [Step 3
SRS]!SRS>0,1,0) AS MissedInPatientAtHand, IIf([Step 3 Patient at Hand
SRS values]!Discrete="Yes" And [Step 3 SRS]!DiscreteScale=
"No",1,0) + IIf([Step 3 Patient at Hand SRS values]!SRS>0 And [Step 3
SRS]!SRS=0,1,0) AS MissedInOthers, [Step 3 Patient at Hand SRS
values].PatientID, [Step 3 SRS].[Patient ID] FROM [Step 3 Patient at
Hand SRS values], [Step 3 SRS];
```

As another embodiment, the similarity score is calculated from the number of features matched:

```
SELECT [Step 4 Number matched].PatientID, [Step 4 Number
matched].[Patient ID], + [Step 4 Number matched]!MatchedFeatures /
(0.2*[Step 4 Number matched]!MissedInPatientAtHand + 0.8*[Step 4
Number matched]!MissedInOthers + [Step 4
Number matched]!MatchedFeatures) AS
SimilarityScore FROM [Step 4 Number matched];
```

5. Calculate outcomes for each patient in the EHR.

For some patients, data on outcomes are not available. Thus, inferences should be made based on patient's compliance with prescribed medication.

As an embodiment, the following SQL commands show how the number of days of medication use is derived from a database containing pharmacy refill orders:

```
SELECT MedicationOrdersFilled.PatientID,
MedicationOrdersFilled.MedicationType,
MedicationOrdersFilled.MedicationDose, Last([Date])-First([Date]) AS
DaysOfCompliance, First(MedicationOrdersFilled.Date) AS FirstOfDate,
Last(MedicationOrdersFilled.Date) AS LastOfDate FROM
MedicationOrdersFilled GROUP BY MedicationOrdersFilled.PatientID,
MedicationOrdersFilled.MedicationType,
MedicationOrdersFilled.MedicationDose;
```

It should be noted that the analysis here assumes that the database includes all or nearly all refill orders.

6. Calculate the expected outcome for the patient at hand.

Expected outcomes can be calculated based on the weighted sum of outcomes. As an embodiment, if the number of records in a pooled database is "n" and the outcome observed for case "j" using medication "m" is "$O_{j,m}$", then the predicted outcome for medication "m" is calculated as a weighed sum of outcomes of similar cases with the same medication.

In essence, $$O_m = \frac{\sum_{j=1,\ldots,n} S_{i,j} O_{j,m}}{\sum_{j=1,\ldots,n} S_{i,j}} \quad (4)$$

Each case in the database can be weighed based on its similarity to the case at hand. As more cases in the pooled database are judged to be similar to the case at hand, a more precise estimate of potential outcomes can be obtained.

It should be noted that in this approach the entire genetic profile (or a large group of likely genes and proteins) is used to establish similarity of two patients. In this sense, no single biomarker is identified.

In contrast, the scientist needs to know why a medication would work for some patients and not others. That scientist would need to search for the genetic markers that predict the efficacy of the medication. The point is that the objectives of translational and scientific investigations lead to different methods of analysis. Hence, one searches for a biomarker relevant to all patients, whereas the other searches for a persistent solution for a single patient.

The following embodiment shows an example of an SQL code for calculating an expected outcome for the patient at hand if such patient were to receive different medication types and doses:

```
SELECT [Step 5 Patients Days of Compliance].MedicationType, [Step 5
Patients Days of Compliance].MedicationDose,
Round(Sum([SimilarityScore]*[DaysOfCompliance])/
(Sum([SimilarityScore])+0.001),2) AS ExpectedDaysOfCompliance
FROM [Step 4 Similarity score] INNER JOIN [Step 5 Patients Days of
Compliance] ON [Step 4 Similarity score].[Patient ID] =
[Step 5 Patients Days of Compliance].PatientID GROUP BY [Step 5
Patients Days of Compliance].MedicationType, [Step 5 Patients Days of
Compliance].MedicationDose;
```

Using results of this calculated process, a clinician may be able to make an informed choice for the patient.

As described further below, the medical outcome prediction tool may also incorporate variations and be applied in different settings.

Depression Example

Patients diagnosed with clinical depression often change their first prescribed medication. This modification generally occurs despite clinician's best effort to recommend medication based on the patients' characteristics. Each time a new medication is tried, one may have to wait (e.g., about six weeks) to see any result of effectiveness. Since for some patients, more than ten different medications may be administered prior to finding an optimal drug, this experimental time period may be lengthy. As a result, significant life-changing events may occur, such as suicide or attempted suicide. Some may abandon management or refuse continued medical attention. Others may even seek an alternative solution, such as using over-the-counter remedies, which may further complicate illness management.

It is important to anticipate a patient's responsiveness to various antidepressants that may shorten the trial-and-error period. Many patients inadvertently or intentionally stop taking their antidepressants. Often, such patients need to medicate themselves through increased drug use.

There are many causes for medication noncompliance. Nonlimiting examples include patient factors (e.g., lack of knowledge about the disease, lack of motivation, lack of self-esteem, lack of a positive patient-physician relationship, etc.), treatment factors (e.g., complexity of treatment, side effects, clinician-patient discord, etc.) lifestyle factors and other demographic factors (e.g., age, marital status, homelessness, lack of support, etc.). One way to improve compliance is to provide patients with medication that they find to be beneficial without the side effects they are trying to avoid.

Many factors can affect patients' reaction(s) to antidepressants, one of which is the patient's genes. It is well known that identified important enzymes (such as CYP2D6, CYP2C19, CYP3A4 and CYP1A2) can metabolize different antidepressant drugs. Tricyclic antidepressants are generally hydroxylated by cytochrome CYP2D6. The tertiary amines, such as amitriptyline, clomipramine and imipramine, are also N-demthylated to the active metabolites, nortiptyline, N-desmethylclomipramine and desipramine, by several CYPs, including the polymorphic CYP2C19, CYP1A2 and CYP3A4. The five selective serotonin reuptake inhibitors flouxetine, fluvoxamine, and paroxetine are partially metabolized by CYP2D6, while citalopram is utilized by CYP2C19. Paroxetine and fluoxetine are very potent inhibitors of CYP2D6 while citalopram, fluvoxamine and sertraline are moderate inhibitors of this enzyme. Fluvoxamine is a potent inhibitor of CYP1A2 and CYP2C19 and a moderate inhibitor of CYP2C9. Data on allelic states of the genes encoding for these enzymes are important, but are unlikely to be sufficient to predict a patient's response to depression medication.

Outcomes depend on a host of other factors besides enzymes. As pointed out by DeVane, CL, factors of clinical importance include "the patient's clinical state, co-administered drugs, therapeutic index, and the relative importance of the defective pathway in the total process of drug elimination."

It should also be noted that despite considerable progress in genotyping patients for depression medication (e.g., even dosage recommendations can be based on genotype), there tends to be a number of unknowns that hamper effective tailoring of patient's medication to their type.

In practice, genotype data are not likely to be available on many patients, and therefore, surrogate measures (e.g., age, race, nationality, previous illness, etc.) should be used as possible predictors of a patient's genotype markers and reaction to antidepressants. For example, data show that men and women differ in their reaction to antidepressants. Age also matters. Furthermore, whites differ from blacks in their reaction to various antidepressants. Even within a race, wide variation in reaction to antidepressants could be anticipated as blacks from South Africa and blacks from other places differ in their reaction to antidepressants. Reviews of literature identify a large number of factors that predict a reaction to antidepressants.

Using the population data, specific recommendations for the patient can be derived. In this example, a patient's reaction to antidepressants is anticipated by identifying similar patients in the entire database. Similar patients are identified by matching the patient on various characteristics known to affect a reaction to antidepressants. Nonlimiting examples of these characteristics include age, sex, race, ethnicity, country of origin, other demographics, disease history, current medications, history of certain medications, and allergies. These should be readily available through the EHR. A large number of patient's characteristics (e.g., typically 30-50 features) may be used to weight each patient in the EHRs. Patients who are more similar to the patient at hand are weighted more heavily. A weighted rate of success for different antidepressants may be calculated. In this manner, population data is used to track and report the likely outcome for the patient at hand. Because this approach does not rely on the average findings in the literature, treatments identified by this approach generally work for the specific patient at hand. However, it is not expected to work on average.

The foregoing descriptions of the embodiments of the present invention have been presented for purposes of illustration and description. They are not intended to be exhaustive or be limiting to the precise forms disclosed, and obviously many modifications and variations are possible in light of the above teaching. The illustrated embodiments were chosen and described in order to best explain the principles of the present invention and its practical application to thereby enable others skilled in the art to best utilize it in various embodiments and with various modifications as are suited to the particular use contemplated without departing from the spirit and scope of the present invention. In fact, after reading the above description, it will be apparent to one skilled in the relevant art(s) how to implement the present invention in alternative embodiments. Thus, the present invention should not be limited by any of the above described example embodiments. Rather, the present invention can also apply to non-medical situations, such as strategic planning, housing development, insurance and other policy decisions, etc.

In addition, it should be understood that any figures, graphs, tables, examples, etc., which highlight the functionality and advantages of the present invention, are presented for example purposes only. The architecture of the disclosed is sufficiently flexible and configurable, such that it may be utilized in ways other than that shown. For example, the steps listed in any flowchart may be reordered or only optionally used in some embodiments.

Further, the purpose of the Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the present invention of the application. The Abstract is not intended to be limiting as to the scope of the present invention in any way.

Furthermore, it is the applicants' intent that only claims that include the express language "means for" or "step for" be interpreted under 35 U.S.C. §112, paragraph 6. Claims that do not expressly include the phrase "means for" or "step for" are not to be interpreted under 35 U.S.C. §112, paragraph 6.

A portion of the present invention of this patent document contains material which is subject to copyright protection. The copyright owner has no objection to the facsimile reproduction by anyone of the patent document or the patent invention, as it appears in the Patent and Trademark Office patent file or records, but otherwise reserves all copyright rights whatsoever.

REFERENCES

F. Alemi, Tukey's Control Chart, 13 QUAL. MGMT. HEALTH CARE 216-21 (2004).

F. Alemi and D. Neuhauser, Time-between Control Charts for Monitoring Asthma Attacks, 30 J. Comm'n J. Qual. Safety 95-102 (2004).

P. Armitage. Sequential Medical Trials (John Wiley & Sons, New York, 2d. ed.) (1975).

K. Brosen, Some Aspects of Genetic Polymorphism in the Biotransformation of Antidepressants, 59 Therapie 5-12 (2004).

J. K. Cuddeback, Why Do (Many) Health IT Projects Fail?, Invited Lecture at Geo. U. (Jul. 12, 2007).

C. L. DeVane, Pharmacogenetics and Drug Metabolism of Newer Antidepressant Agents, 55 J. Clinical Psychiatry 38-45 (Supp. 1994).

A. Doris et al., Depressive Illness, 354 Lancet 1369-75 (1999).

E. B. Elbogen et al., Medication Nonadherence and Substance Abuse in Psychotic Disorders: Impact of Depressive Symptoms and Social Stability, 193 J. Nervous & Mental Disease 673-79 (2005).

C. Evans and S. T. Ildstad, Small Clinical Trials: Issues and Challenges (Inst. Med. Nat'l Acad. Press) (2001).

W. E. Evans and M. V. Relling, Pharmacogenomics: Translating Functional Genomics into Rational Therapeutics, 286 Sci. 487-91 (1999).

D. F. Heitjan, Bayesian Interim Analysis of Phase II Cancer Clinical Trials, 16 Stat. Med. 1791-1802 (1997).

J. Kirchheiner et al., CYP2D6 and CYP2C19 Genotype-Based Dose Recommendations for Antidepressants: A First Step Towards Subpopulation-Specific Dosages, 104 Acta Psychiatrica Scandinavica 173-92 (2001), erratum in 104 Acta Psychiatrica Scandinavica 475 (2001).

N. Kleindienst et al., Psychosocial and Demographic Factors Associated with Response to Prophylactic Lithium: A Systematic Review for Bipolar Disorders, 35 Psychol. Med. 1685-94 (2005).

P. H. Kuo et al., The Temporal Relationship of the Onsets of Alcohol Dependence and Major Depression: Using a Genetically Informative Study Design, 36 Psychol. Med. 1153-62 (2006).

S. Naito et al., Gender Differences in the Clinical Effects of Fluvoxamine and Milnacipran in Japanese Major Depressive Patients, 61 Psychiatry Clinical Neurosci. 421-27 (2007).

D. Neuhauser, Why Design of Experiments Just May Transform Health Care, 14 Qual. Mgmt. Health Care 217-18 (2005).

G. I. Papakostas et al., Relative Antidepressant Efficacy of Bupropion and the Selective Serotonin Reuptake Inhibitors in Major Depressive Disorder: Gender-Age Interactions, 22 Int'l Clinical Psychopharmacology 226-29 (2007).

A. Raskin and T. H. Crook, Proceedings: Race and Response to Antidepressant Drugs in Hospitalized Depressed Patients, 10 Psychopharmacology Bull. 67 (1974).

A. Rifkin et al., Possible Effect of Race on Tricyclic Plasma Levels, 239 J. Am. Med. Ass'n 1845-46 (1978).

I. Ritov et al., Differential Weighting of Common and Distinctive Components, 119 J. Experimental Psychol. 30-41 (1990).

F. Rosner, Patient Noncompliance: Causes and Solutions, 73 Mt. Sinai J. Med. 553-59 (2006).

W. Steimer et al., Pharmacogenetics: A New Diagnostic Tool in the Management of Antidepressive Drug Therapy, 308 Clinica Chimica Acta 33-41 (2001).

P. H. Thall, New Statistical Strategy for Monitoring Safety and Efficacy in Single-Arm Clinical Trials, 14 J. Clinical Oncology 296-303 (1996).

I. Truter and T. J. Kotze, An Investigation into the Prescribing Patterns of Selective Serotonin Re-uptake Inhibitors in South Africa, 21 J. Clinical Pharm. Therapeutics 237-42 (1996).

A. Tversky, Features of Similarity, 84 Psychological Rev. 327-352 (1977).

T. Verguts et al., Measures of Similarity in Models of Categorization, 32 Memory Cognition 379-89 (2004).

What is claimed is:

1. A medical outcome prediction tool encoded with instructions in a tangible computer readable medium for predicting an individual's medical outcomes from at least one computer database storing electronic medical data for a patient population, wherein execution of the instructions by one or more processors causes the one or more processors to perform the steps comprising:
   a. identifying patients within a patient population having a same disease from electronic health records in at least one computer database;
   b. selecting a set of characteristics from the electronic health records that is unique to an individual among the identified patients;
   c. determining the similarities between the individual and other cases among the identified patients by:
      i. calculating the number of matches between the individual and the cases over the set of characteristics; and
      ii. using the result of the calculated matches to determine a similarity score; and
   d. calculating an expected outcome for the individual by:
      i. generating a result by summing the product between the similarity score and a weighted sum of outcomes; and
      ii. dividing the result by the sum of the similarity score.

2. The medical outcome prediction tool according to claim 1, further including the step of calculating outcomes from the cases that are compliant with medication.

3. The medical outcome prediction tool according to claim 1, wherein the number of matches between the individual and the cases over the set of characteristics are calculated by:
   a. using a standardized and rounded scale (SRS) value, wherein the SRS value is the difference of an observed value of at least one of the characteristics and an average of at least one of the characteristics, and the difference being:
      i. divided by a standard deviation of at least one of the characteristics; and
      ii. rounded; and
         wherein the individual and the cases have a matching characteristic if both the individual and the cases have the same SRS value; and
   b. using the result of the calculated matches to determine a similarity score, wherein the similarity score comprises: dividing the number of the characteristics matched between the individual and the cases by the sum of the number of the characteristics matched between the individual and the cases plus a weighted sum of number of nonmatched characteristics, wherein the weighted sum comprises:
      i. a number of the characteristics in the individual but not in the cases; and
      ii. a number of the characteristics in the cases but not in the individual.

4. A medical outcome prediction method for predicting an individual patient's medical outcomes, the method comprising:
   a. identifying patients within a patient population having a same disease from electronic health records in at least one computer database;
   b. selecting a set of characteristics from the electronic health records that is unique to an individual among the identified patients;
   c. determining the similarities between the individual and other cases among the identified patients by:
      i. calculating the number of matches between the individual and the cases over the set of characteristics; and
      ii. using the result of the calculated matches to determine a similarity score; and
   d. calculating an expected outcome for the individual by:
      i. generating a result by summing the product between the similarity score and a weighted sum of outcomes; and
      ii. dividing the result by the sum of the similarity score.

5. The method according to claim 4, further including calculating outcomes from the cases that are compliant with medication.

6. The method according to claim 4, wherein the number of matches between the individual and the cases over the set of characteristics is calculated by:
   a. using a standardized and rounded scale (SRS) value, wherein the SRS value is the difference of an observed value of at least one of the characteristics and an average of at least one of the characteristics, and the difference being:
      i. divided by a standard deviation of at least one of the characteristics; and
      ii. rounded; and
         wherein the individual and the cases have a matching characteristic if both the individual and the cases have the same SRS value; and
   b. using the result of the calculated matches to determine a similarity score, wherein the similarity score comprises: dividing the number of the characteristics matched between the individual and the cases by the sum of the number of the characteristics matched between the individual and the cases plus a weighted sum of number of nonmatched characteristics, wherein the weighted sum comprises:
      i. a number of the characteristics in the individual but not in the cases; and
      ii. a number of the characteristics in the cases but not in the individual.

7. A system for predicting an individual patient's medical outcomes, the system comprising:
   a. a patient-disease identifier, configured for identifying patients within a patient population having a same disease from electronic health records in at least one computer database;
   b. a characteristics identifier, configured for selecting a set of characteristics from the electronic health records that is unique to an individual among the identified patients;
   c. a similarities determiner, configured for determining the similarities between the individual and other cases among the identified patients by:
      i. a matcher, configured for calculating the number of matches between the individual and the cases over the set of characteristics; and
      ii. a similarity scorer, configured for determining a similarity score by using the result of the calculated matches; and
   d. an expected outcome generator, configured for calculating an expected outcome for the individual by:
      i. generating a result by summing the product between the similarity score and a weighted sum of outcomes; and
      ii. dividing the result by the sum of the similarity score.

8. The system according to claim 7, further including an outcome calculator, configured for calculating outcomes from the cases that are compliant with medication.

9. The system according to claim 7, wherein the matcher uses a standardized and rounded scale (SRS) value to calculate the number of matches between the individual and the cases over the set of characteristics, wherein the SRS value is the difference of an observed value of at least one of the characteristics and an average of at least one of the characteristics, and the difference being:
   a. divided by a standard deviation of at least one of the characteristics; and
   b. rounded; and
      wherein the individual and the cases have a matching characteristic if both the individual and the cases have the same SRS value.

10. The system according to claim 7, wherein the similarity score is determined by: dividing the number of the characteristics matched between the individual and the cases by the sum of the number of the characteristics matched between the individual and the cases plus a weighted sum of number of nonmatched characteristics, wherein the weighted sum comprises:
   a. a number of the characteristics in the individual but not in the cases; and
   b. a number of the characteristics in the cases but not in the individual.

* * * * *